(12) United States Patent
McGaffigan

(10) Patent No.: US 6,887,237 B2
(45) Date of Patent: May 3, 2005

(54) METHOD FOR TREATING TISSUE WITH A WET ELECTRODE AND APPARATUS FOR USING SAME

(75) Inventor: Thomas H. McGaffigan, Saratoga, CA (US)

(73) Assignee: Medtronic, Inc., Minneapolis, MN (US)

( * ) Notice: Subject to any disclaimer, the term of this patent is extended or adjusted under 35 U.S.C. 154(b) by 126 days.

(21) Appl. No.: 10/201,502

(22) Filed: Jul. 22, 2002

(65) Prior Publication Data

US 2004/0015162 A1 Jan. 22, 2004

(51) Int. Cl.$^7$ ............................................... A61B 18/18
(52) U.S. Cl. .................... 606/41; 607/101; 607/105; 606/34
(58) Field of Search .................. 606/31–34, 41, 606/42; 607/101–105

(56) References Cited

U.S. PATENT DOCUMENTS

| | | | | |
|---|---|---|---|---|
| 5,334,193 A | * | 8/1994 | Nardella ...................... | 606/41 |
| 5,370,675 A | | 12/1994 | Edwards et al. ............ | 607/101 |
| 5,403,311 A | * | 4/1995 | Abele et al. ................. | 606/49 |
| 5,421,819 A | | 6/1995 | Edwards et al. ............. | 604/22 |
| 5,549,644 A | | 8/1996 | Lundquist et al. ........... | 604/22 |
| 5,554,172 A | * | 9/1996 | Horner et al. ................ | 607/88 |
| 5,562,721 A | * | 10/1996 | Marchlinski et al. ......... | 607/99 |
| 5,769,880 A | * | 6/1998 | Truckai et al. .............. | 607/101 |
| 5,807,395 A | | 9/1998 | Mulier et al. | |
| 5,964,756 A | | 10/1999 | McGaffigan et al. ......... | 606/41 |
| 6,016,809 A | | 1/2000 | Mulier et al. ............... | 128/898 |
| 6,238,393 B1 | * | 5/2001 | Mulier et al. ................ | 606/41 |
| 6,409,722 B1 | * | 6/2002 | Hoey et al. .................. | 606/34 |
| 6,638,275 B1 | | 10/2003 | McGaffigan et al. ......... | 606/41 |
| 2002/0019628 A1 | | 2/2002 | Comben | |

FOREIGN PATENT DOCUMENTS

| | | |
|---|---|---|
| EP | 0 878 167 A | 11/1998 |
| WO | WO 00/09208 | 2/2000 |

OTHER PUBLICATIONS

Djavan et al. "Transurethral Radiofrequency Therapy for Benign Prostatic Hyperplasia Using a Novel Saline–Liquid Conductor: The Virtual Electrode" Urology, vol. 55, 2000, pp. 13–16.

* cited by examiner

*Primary Examiner*—Michael Peffley
(74) *Attorney, Agent, or Firm*—IPLM Group, P.A.

(57) ABSTRACT

A method for treating tissue of a mammalian body in which the conductivity of the tissue is characterized. The amount of a conductive liquid to supply to the tissue is determined as a function of the conductivity of the tissue and injected into the tissue over an interval of time. Electromagnetic energy is supplied to the tissue to form a lesion in the tissue. A computer-readable memory and a radio frequency generator and controller utilizing such method are further provided.

14 Claims, 8 Drawing Sheets

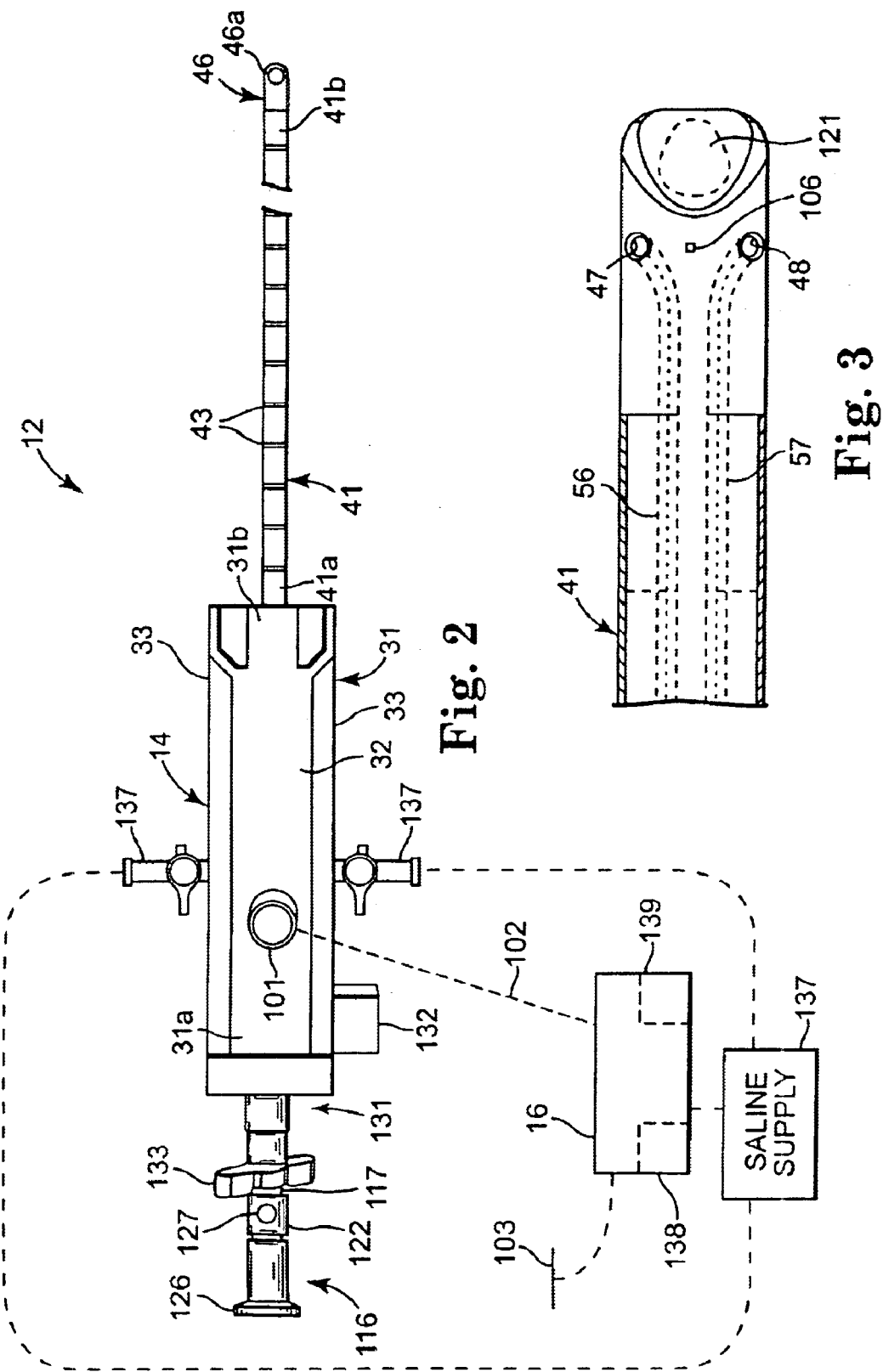

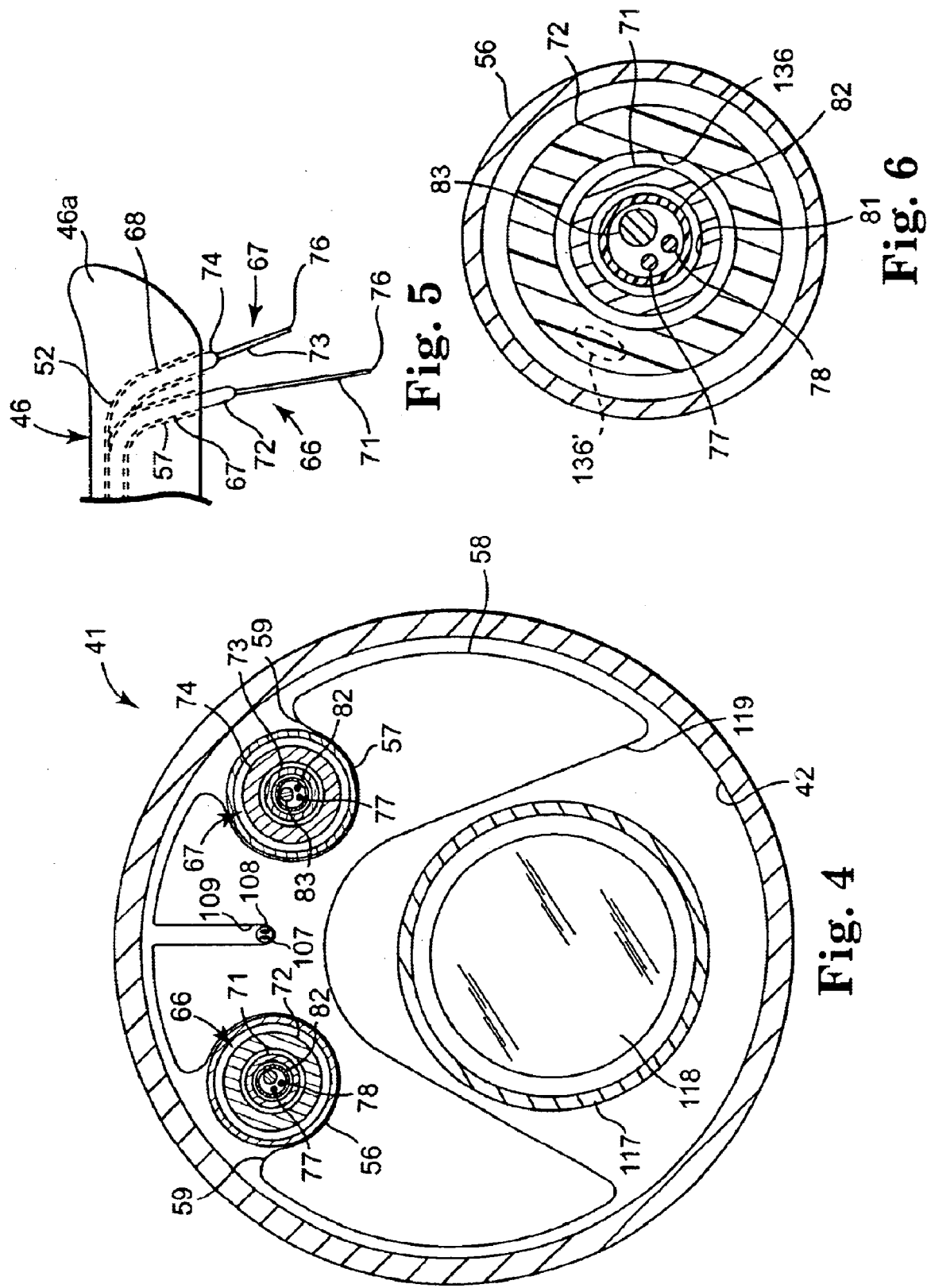

US 6,887,237 B2

METHOD FOR TREATING TISSUE WITH A WET ELECTRODE AND APPARATUS FOR USING SAME

FIELD OF THE INVENTION

This invention pertains generally to methods and apparatus for treating tissue and, more particularly, to methods and apparatus for treating tissue utilizing a wet electrode.

BACKGROUND

Medical devices have been provided for treating benign prostatic hyperplasia by the use of radio frequency energy. See, for example, U.S. Pat. Nos. 5,370,675, 5,421,819 and 5,549,644. Radio frequency energy passing from an electrode of such a device through the adjoining tissue causes heating of the tissue. In order to cause tissue ablation and subsequent necrosis, the treated tissue is heated to a temperature in excess of 47° C.

Radio frequency generators can be provided with power levels up to several hundred watts for accomplishing such ablation and necrosis. Unfortunately, the amount of power that can practically be delivered to a patient is limited by physiological factors. For example, when a patient is unconscious under a general anesthetic, a few hundred watts of radio frequency power can be delivered for short periods of time. The amount of power that can be delivered to a conscious patient is under a hundred watts.

Some of the previously provided medical devices permit a liquid to be introduced into an area adjacent a conductive electrode. See in this regard U.S. Pat. Nos. 5,370,675 and 5,421,819. Other devices have been provided for introducing a conductive liquid through an electrode into tissue to be ablated. See, for example, U.S. Pat. No. 6,016,809. Prior art lesion producing devices utilizing an infused conductive liquid have failed to recognize the importance of maintaining a specific range of current density distributed over the effective electrode area.

It would be desirable to produce a predictable necrotic lesion with a minimum amount of power.

SUMMARY OF THE INVENTION

A method for treating tissue of a mammalian body has been provided in which the conductivity of the tissue is characterized. The amount of a conductive liquid to supply to the tissue is determined as a function of the conductivity of the tissue and injected into the tissue over an interval of time. Electromagnetic energy is supplied to the tissue to form a lesion in the tissue. A computer-readable memory and a radio frequency generator and controller utilizing such method are further provided.

BRIEF DESCRIPTION OF THE DRAWINGS

FIG. 2 is a top elevational view of the apparatus of FIG. 1 taken along the line 2—2 of FIG. 1.

FIG. 3 is a bottom elevation view of a portion of the apparatus of FIG. 1 taken along the line 3—3 of FIG. 1.

FIG. 4 is a cross-sectional view of the apparatus of FIG. 1 taken along the line 4—4 of FIG. 1.

FIG. 5 is an enlarged view of the distal extremity of the apparatus of FIG. 1 wherein the first and second stylets of the apparatus are partially deployed.

FIG. 6 is an enlarged cross-sectional view of a portion of the apparatus shown in FIG. 4.

DESCRIPTION OF THE INVENTION

Figure 1:
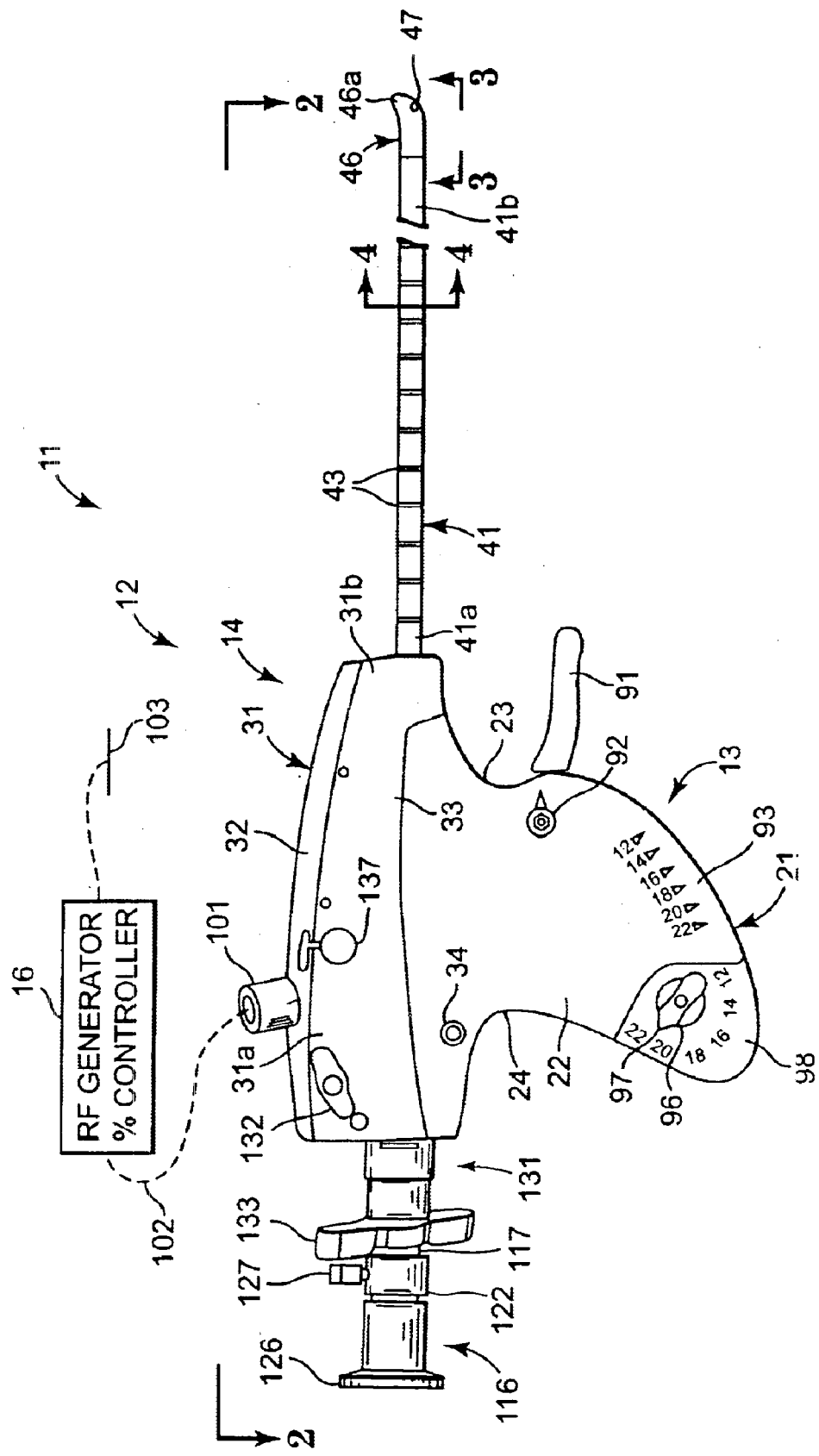
FIG. 1 is a side elevational view of an apparatus for creating a wet electrode of the present invention.

The method and apparatus of the present invention are for treating a mammalian body, such as a human patient. Such apparatus is part of a system 11 and can be in the form of a transurethral needle ablation apparatus or device 12 similar to the apparatus shown in U.S. Pat. No. 5,964,756 and in U.S. patent application Ser. No. 09/684,376 filed Oct. 5, 2000, the entire content of each of which is incorporated herein by this reference. Device 12 includes a reusable handle 13 on which there is mounted a detachable cartridge 14. The needle electrodes of the device are supplied with radio frequency energy from a radio frequency generator and controller 16, which can be similar to the type commercially available from Medtronic, Inc. of Minneapolis, Minn. The device 12 is further supplied with a conductive liquid such as a saline solution provided from one or more reservoirs and preferably from a saline supply 17 (see FIG. 2). Controller 16 is preferably coupled to the saline supply 17 to control the output thereof. The method and apparatus of the present invention can be utilized to form a wet electrode of a desired size.

Apparatus 12 is similar in construction to the apparatus disclosed in U.S. Pat. No. 5,964,756. Using that same construction, handle 13 is comprised of a housing 21 which is ergonomically shaped so as to be adapted to fit in a human hand. Specifically, the handle 13 is in the form of a pistol grip which has a main body portion 22 that is provided with a forward indentation 23 adapted to receive the index finger of the human hand grasping the handle 13 and a larger rearwardly facing indentation 24 adapted to receive the thumb of the same human hand. Housing 21 is made from metal or any other suitable material.

Cartridge 14 consists of a cover 31 that is generally U-shaped in cross section and is formed of a suitable material such as plastic. The cover 31 is provided with proximal and distal extremities 31a and 31b and is formed by a curved top wall 32 and depending adjoining spaced-apart parallel side walls 33. A release button 34 is provided on each of the opposite sides of the housing 21 for releasing the removable cartridge 14 from the handle 13.

An elongate tubular member or probe 41 preferably in the form of a rigid torque tube made from any suitable material such as stainless steel is provided and includes proximal and distal extremities 41a and 41b. Probe 41 has its proximal extremity mounted to the distal extremity 31b of cover 31. The tubular torque member 41 has a suitable diameter as for example 18 French and is provided with a passage 42 circular in cross section extending therethrough (see FIG. 3).

The outer surface of the probe 41 is provided with spaced-apart markings 43 which are spaced apart by one centimeter increments to aid the physician in insertion of the probe 41 into the urethra.

A bullet-shaped tip or distal guide housing 46 formed of a suitable plastic transparent to light is secured to the distal extremity of the torque tube or probe 41 in the manner described in U.S. Pat. No. 5,964,756 (see FIGS. 1 and 3). As shown in FIG. 1, the distal tip 46 has an upturned rounded portion 46a. The elongate probe 41 and the tip 46 preferably have a combined length of approximately 9.5 inches. A pair of circumferentially spaced-apart holes 47 and 48 are provided on the underside of the bullet-shaped tip 46 opposite the upturned portion 46a. The first and second holes 47 and 48 are spaced apart from each other by a suitable distance as for example one centimeter, which dimension is determined by the diameter of the torque tube 46 (see FIG. 3). First and second angled guide tubes 51 and 52 which are aligned with the respective first and second holes 47 and 48 have L-shaped 90° bends therein that are molded into the transparent bullet-shaped tip 46. Such 90° bends provided in the first and second angled guide tubes provide transitions from movement through the tubes along a longitudinal axis to movement along a transverse axis extending at 90° with respect to the longitudinal axis.

The first and second angled guide tubes 51 and 52 adjoin straight guide tubes 56 and 57, respectively, which extend through the passage 42 provided in the torque tube or elongate probe 41 (see FIGS. 3 and 4). Each of the straight guide tubes 56 and 57 has a proximal extremity attached to cover 31 and a distal extremity attached to the distal tip 46. As shown particularly in FIG. 4, the straight guide tubes 56 and 57 are supported in predetermined spaced-apart positions in the passage 42 by an insert 58 formed of plastic that is disposed in the torque tube 41 and has spaced-apart recesses 59 formed in the outer periphery of the insert 58. The straight guide tubes 56 and 57 are made from plastic or any other suitable material.

A pair of first and second elongate members or stylets 66 and 67 are slidably mounted in the first and second straight guide tubes 56 and 57 within probe 41 (see FIGS. 4–6). Each of the elongate stylets has a proximal extremity, not shown, disposed in cover 31 and a distal extremity 68 disposed in the distal extremity of probe 41 and tip 46. First stylet 66 is preferably formed from a needle electrode 71 and a layer of insulating material disposed around the needle electrode but exposing a distal portion of the needle electrode. The layer of insulating material is preferably a sleeve 72 slidably mounted on the needle electrode 71. Second stylet 67 is similar in construction to the first stylet 66 and includes a needle electrode 73 and a sleeve 74 slidably mounted on the needle electrode 73. The needle electrodes 71 and 73 are preferably formed of a hollow superelastic nickel-titanium material having an outside diameter of 0.018 inch and an inside diameter of 0.012 inch and a wall thickness of 0.003 inch. The sleeves 72 and 74 are preferably made from plastic or any other suitable insulating material and extend through the guide tubes 51, 52, 56 and 57 so that the entire lengths of the needle electrodes 71 and 73 extending through the passage 42 are insulated from each other and from the torque tube 41. The sheaths or sleeves 72 and 74 additionally provide stiffness to the needle electrodes during penetration of the urethral or other passage wall into which tip 46 is introduced. The insulating sheaths are sized in length so that when the needle electrodes are retracted within the bullet-shaped tip 46, they are substantially covered with the insulation. When the needle electrodes are deployed, the sheaths 72 and 74 continue to cover the needle electrodes, but permit the distal portion of the needle electrodes to be exposed in the targeted tissue. The stylets 66 and 67 have an included angle of approximately 40°.

A suitable temperature sensor is carried by each of the first and second stylets 66 and 67. The distal extremity of each of the needle electrodes is provided with a sharpened tip and has a thermocouple 76 or other suitable temperature sensor mounted within the sharpened tip (see FIG. 5). Each thermocouple is provided with a pair of wires 77 and 78 which extend proximally from the sharpened tip through a longitudinal lumen 81 provided in the hollow needle electrode 71 or 73 (see FIGS. 4 and 6). A separate insulating sleeve 82 is provided in each electrode lumen 81 to provide additional insulation isolating the thermocouple wires from the metal needle electrode. In order to strengthen the needle electrodes 71 and 73 and to inhibit wall collapse and kinking during bending, a nickel-titanium rod 83 is disposed within each internal sleeve 82 alongside the thermocouple wires 77 and 78. Strengthening rod 83 has an external diameter of 0.006 inch and each of the thermocouple wires 77 and 78 has an outside diameter of 0.005 inch. The rod 83 and the thermocouple wires 77 and 78 are cemented in place by a suitable polyurethane adhesive (not shown).

Handle 13 and cartridge 14 are provided with internal mechanisms much the same as described in U.S. Pat. No. 5,954,756, wherein the operation of such mechanisms are described in detail. In general, such mechanisms are adapted to be operated by a needle and sheath deployment and retraction trigger 91 that is adapted to be engaged by the forefinger of the hand holding the body portion of the housing 21 (see FIG. 1). The trigger 91 is adapted to be moved from a "load" position indicated by the arrow 92 through a plurality of deployed positions indicated by indicia 93 ranging from 12 to 22 millimeters provided on opposite sides of the housing 21. In this regard, actuation of the trigger 91 initially causes the first and second stylets 66 and 67 to slidably deploy from respective guide tubes 51 and 56 and 52 and 57 so as to extend sidewise in unison from the distal tip. Further downward movement of the trigger 91 causes the insulating sleeves 72 and 74 to retract a predetermined amount relative to the respective needle electrodes 71 and 73. The length of the resulting tissue penetration of stylets 66 and 67 is determined by the position of an interconnected pair of knobs 96, which set stops for limiting movement of the trigger 91 so that overtravel beyond the setting provided by the knobs 96 cannot occur. The interconnected knobs 96 are provided on opposite sides of the housing 21 adjacent the lower extremity of the body 21 and have pointers 97 movable over indicia 98 ranging from 12 to 22 millimeters in the same increments as the indica 93. The indicia 98 indicate the length of penetration of the needle electrodes 71 and 73, for example through the urethral wall and into the prostatic tissue of the prostate. Sleeves or sheaths 72 and 74 are retracted a predetermined amount as for example six millimeters relative to the needle electrodes so that there is exposed approximately six millimeters of the needle electrodes in the targeted tissue with the insulating sheaths still extending through the urethral or other passage wall so as to protect such wall during RF ablation of the targeted tissue.

Generator and controller 16 is electrically coupled to the first and second stylets 66 and 67, and specifically to the first and second needle electrodes 71 and 73. In this regard, an electrical connector 101 is provided on cover 31 for permitting electrical communication between the generator 16 and the proximal extremity of the needle electrodes. Controller is electrically coupled to connector 101 by means of a cable 102 or other suitable lead. The generator 16 is provided with two channels of radio frequency energy, making it possible to deliver different amounts of power to two or more different needle electrodes which are typically operated in a monopolar fashion utilizing a return or dispersive electrode 103 adhered to the small of the back of the patient. The proximal ends of first and second thermocouple wires 77 and 78 are also electrically coupled to connector 101 for permitting controller 16 to monitor temperatures sensed thereby.

A temperature sensor such as a thermocouple 106 is encapsulated in the bullet-shaped tip 46 and, as shown in FIG. 3, is disposed in the vicinity of stylet openings 47 and 48 provided in the tip. Thermocouple 106, which permits the sensing of urethral wall temperatures, is connected to wires 107 and 108 extending through the passage 42 and is supported in a recess 109 in the insert 58 (see FIG. 4). The wires 107 and 108 are electrically connected within cover 31 to connector 101 for permitting the monitoring of the readings obtained thereby by generator and controller 16. The thermocouple 106 is used to ensure that the highest temperature reached in the urethra does not exceed approximately 47° C. Such hottest location is typically found between the needle pairs 71 and 73 and it is for this reason that the thermocouple 106 is so located.

The cover 31 and the torque tube 41 are sized to receive a conventional telescope or scope 116 which includes a tubular member 117 having a rod lens 118 and fiber optics (not shown) surrounding the rod lens (see FIGS. 1 and 2). The scope 116 is movable through the cover 31 and a recess 119 provided in the insert 58 disposed in the passage 72 of the tube 41 and thence into a bore 121 provided in the bullet-shaped tip 46 (see FIG. 3). The bore 121 is in alignment with the recess 119 provided in the torque tube 41. When the distal extremity of the tubular member 117 is positioned within the bore 121, it is possible to view the surrounding region through the transparent tip 46 because the tip 46 has an index of refraction which is similar to the surrounding liquid, such as saline solution, within the urethra or other body passage into which probe 41 has been placed. A fitting 122 is provided on the proximal extremity of the tubular member 117 and includes an eyepiece 126 and a connector 127 for making connection to a fiber optic light source (not shown).

In order to permit movement of the scope 116 into position so that the physician can also observe independently deployment of the first and second needle electrodes 71 and 73, means is provided for causing longitudinal movement of the scope 116 relative to the torque tube 41 (see FIGS. 1 and 2). To this end telescope moving means 131, described in detail in copending patent application Ser. No. 09/684,376 filed Oct. 5, 2000 is provided in the proximal extremity 31a of cover 31. In general, the telescope moving means 131 includes a telescope positioning knob 132 extending from one of the side walls 33 of cover 31 and a scope locking lever 133. Release button 34, and the internal mechanisms and operation thereof, are also described in copending patent application Ser. No. 09/684, 376 filed Oct. 5, 2000.

Each of the first and second stylets 66 and 67 has a lumen extending from the proximal extremity to the distal extremity of the stylet for permitting a conductive or other fluid to be introduced by apparatus 12 into the tissue being treated. The lumen can be provided in any portion of the stylet and can be in the form of a lumen extending through the needle electrode or through the insulating sleeve. In one preferred embodiment, and as shown in the drawings, each of the insulating sleeves 72 and 74 is provided with a lumen 136 extending longitudinally therethrough. As shown in FIG. 6, the lumen can be an annular lumen 136 extending around the respective needle electrode and permitted by sizing the internal diameter of the insulating sleeve larger than the external diameter of the needle electrode. Alternatively, or in addition, the lumen can be in the form of one or more lumens 136', one of which is shown in dashed lines in FIG. 6, which are offset from the central lumen of the sleeve 72. Where more than one lumen 136' is provided, such lumens can be spaced circumferentially or otherwise about the insulating sleeve.

The lumen 136 is accessible from the proximal extremity of the respective stylet and reservoir 17 of a suitable conductive liquid such as saline is coupled to the proximal extremity of each stylet for supplying such liquid to the tissue targeted by apparatus 12 (see FIG. 2). One or more suitable fluid connectors 137 are provided on apparatus 12 for permitting fluid communication between reservoir or saline supply 17 and sleeve lumens 136. In the illustrated embodiment of the invention, first and second fluid connectors in the form of first and second stopcocks 137 extend from the opposite side walls 33 of the cover 31 and connect to saline supply 17 by means of suitable lines or tubing, shown in dashed lines in FIG. 2.

As discussed above, control apparatus 16 includes means coupled to the radio frequency generator thereof and thermocouple 76 for characterizing the conductivity of the tissue being treated. More specifically, both the electrical and thermal conductivity of the tissue are characterized. In addition, the control apparatus 16 includes means as a function of the conductivity of the tissue for determining the amount of the conductive liquid to supply to the tissue, and specifically the rate of infusion of the conductive fluid, for forming a wet electrode. In this regard, controller 16 includes a computer having a central processing unit or processor 138 and memory 139 electrically coupled to the processor. The computer is programmed, for example by software, for controlling the operation of processor 138. Included in the computer memory 139, such as in a look-up table, is information which permits characterization of the conductivity of the tissue being treated and the size of the wet electrode to be created in the tissue.

Figure 7:
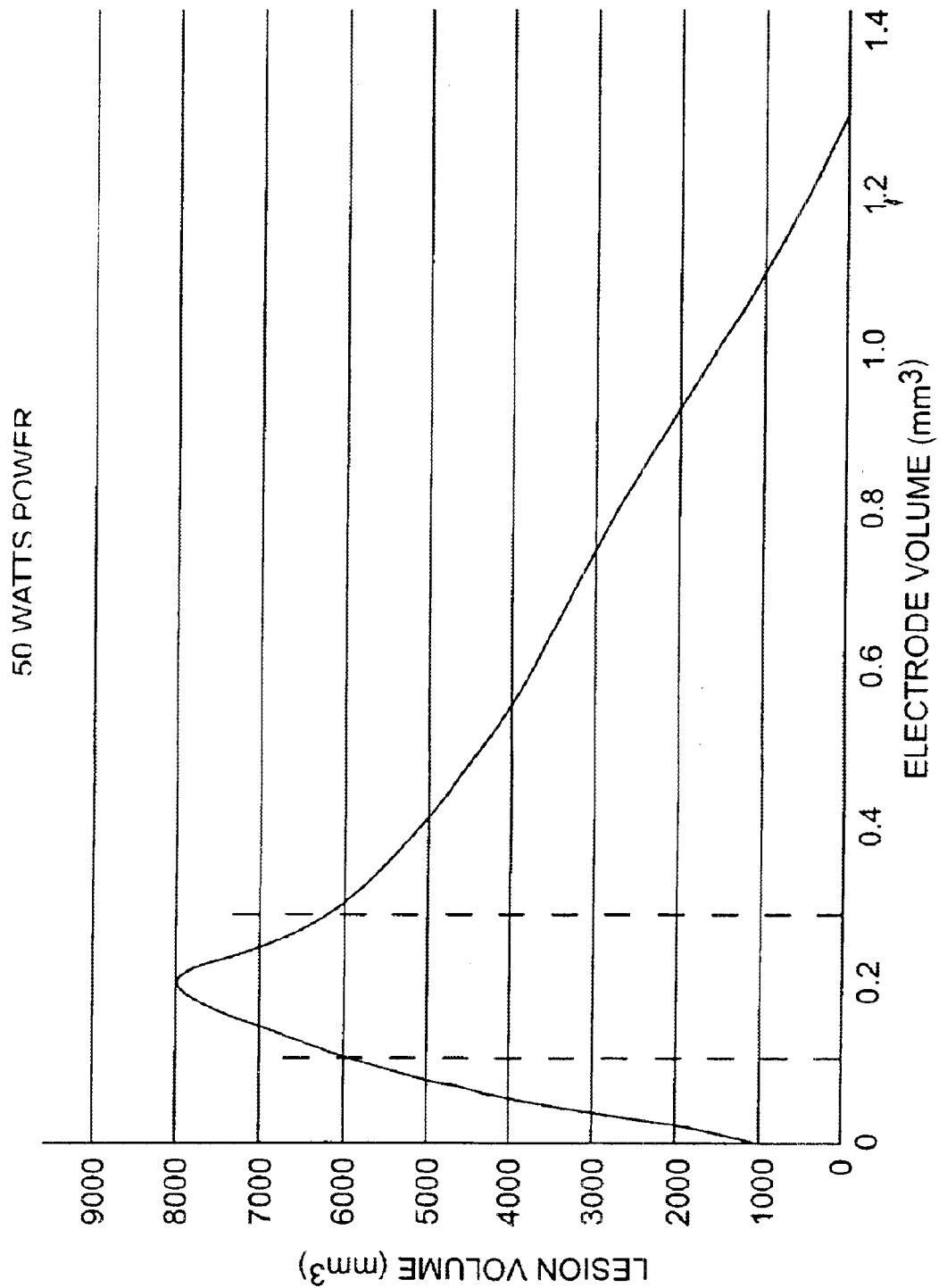
FIG. 7 is an exemplary graph of lesion volume as a function of electrode volume for use in the method of the present invention.

With respect to the foregoing, the computer memory 139 can be programed with information for a variety of targeted tissues having varying electrical and thermal conductivities. In this regard, FIG. 7 shows an exemplary graph of the volume of a lesion created in tissue versus electrode volume of a radio frequency electrode where 50 watts of power was delivered to said electrode. Such power delivery was continuous except where power cutoffs were triggered due to excessive impedance levels. The information of FIG. 7 was taken from several tests performed on turkey breasts, with the electrode volume being created by inserting a needle electrode of the type set forth above into a plurality of brass spheres of varying volumes and a similar power provided to each of such needles and sleeves.

As can be seen from FIG. 7, a suitable lesion volume ranging from 6000 to 8000 cubic millimeters occurs when the electrode volume ranges from approximately 0.1 to 0.3 cubic millimeters. The lesion volume is optimized at a value of approximately 8000 cubic millimeters when the electrode has a volume of approximately 0.2 cubic millimeters. Current densities on the outer surface of the electrode are similarly desirable at electrode volumes ranging from 0.1 to 0.3 cubic millimeters and optimized for electrode volumes of approximately 0.2 cubic millimeters. The lesion volume of FIG. 7 drops off significantly below an electrode volume of approximately 0.2 cubic millimeters due to the high current densities and resulting high impedances created by such small electrode volumes. Electrical impedances above a certain level inhibit and ultimately preclude the travel of radio frequency through the prostatic tissue, thus limiting the size of the resulting lesion. The lesion volume falls off above approximately 0.2 cubic millimeters as a result of the continuing decrease in current density with increased electrode volume for a given power.

A graph similar to that shown in FIG. 7 can be created for power levels other than 50 watts. In this regard, the curve of FIG. 7 scales upwardly or downwardly as function of the delivered power. In addition, the graph of FIG. 7 is dependent on the impedance of the electrode circuit, that is the circuit between the radio frequency generator and controller 16 and the return electrode 103. The portion of such circuit which typically contributes to impedance change is the portion of the circuit created by the human body being treated, more specifically the portion of the body between the active needle electrode 71 or 73 and the return electrode 103. Such portion of the body includes, for example, prostatic tissue where the treatment is involves treating the prostate. In general, the impedance of such portion of the electrode circuit is proportional to the distance between the active needle electrode and the return electrode. Any scaling of the graph of FIG. 7 due to power or impedance variations is along the y axis, that is the axis depicting the size of the lesion volume, and not along the x axis. Accordingly, the optimized electrode volume of approximately 0.2 cubic millimeters shown in FIG. 7 would not change as a result of any such scaling.

Where the patient to be treated is a human male, a graph similar to that of FIG. 7 would be created from one or more prostates of cadavers and the optimized electrode volume stored in the memory 139 of controller 16. The power levels and impedance levels utilized in creating such graph, including the impedance created by the distance between the active and return electrodes, should approximate the power levels expected to be utilized and the impedance levels expected to exist during the treatment. Although a plurality of optimized electrode volumes as a function of prostatic tissue types could be stored in the computer memory 139, in one preferred embodiment it is anticipated that the variations in such optimized electrode volumes from human to human are relatively insignificant and thus only a single optimized electrode volume is stored in the computer memory for prostatic tissue.

Figure 8:
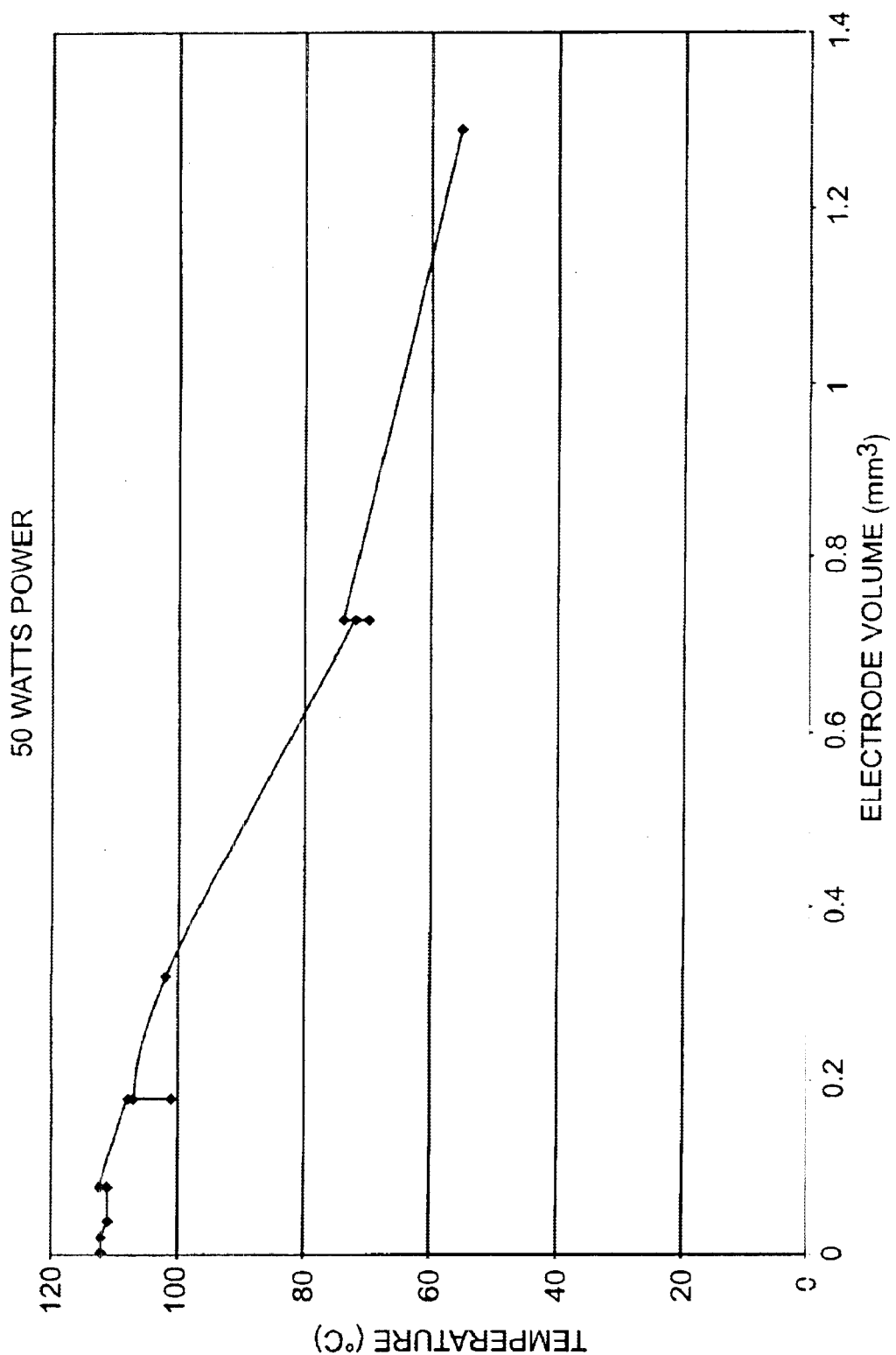
FIG. 8 is an exemplary graph of temperature as a function of electrode volume for use in the method of the present invention.

In FIG. 8, the temperature monitored by thermocouple 76 is graphed as a function of the volume of the radio frequency electrode for the case where 50 watts of power was delivered to said electrode. As with the information of FIG. 7, such power delivery was continuous except where power cutoffs were triggered due to excessive impedance levels. As shown therein, desirable tissue temperatures between 100° C. and 120° C. and preferably between 100° C. and 110° C. are achieved when the electrode volume is approximately 0.3 cubic millimeters or less. When the electrode volume is greater than approximately 0.3 cubic millimeters, the reducing current densities on the increasing electrode surface area provide tissue temperatures that are too cold to optimize lesion creation. Although FIG. 8 shows that electrode volumes below 0.1 cubic millimeters provide suitable tissue temperatures for lesion creation, FIG. 7 discussed above shows that lesion volumes decrease below approximately 0.2 cubic millimeters. In this regard, the tissue temperatures for electrode volumes below approximately 0.1 cubic millimeters are restricted by undesirably high impedances which limit further resistive heating of the tissue. FIG. 8 confirms that electrode volumes ranging from 0.1 to 0.3 cubic millimeters and preferably approximately 0.2 cubic millimeters are desirable.

Similar to the discussion above with respect to FIG. 7, the graph of FIG. 8 scales along the y axis, but not along the x axis, with changes in delivered power and changes in the impedance of the electrode circuit. In addition and like FIG. 7, the information of the exemplary FIG. 8 was taken from turkey breasts. A graph similar to FIG. 7 would be prepared from one or more human prostates or other tissue being treated and stored in the memory 139 of controller 16. The empirical data for creating such similar graph would be acquired under power and impedance conditions which approximate the procedure in which such graph would be utilized.

Figure 9:
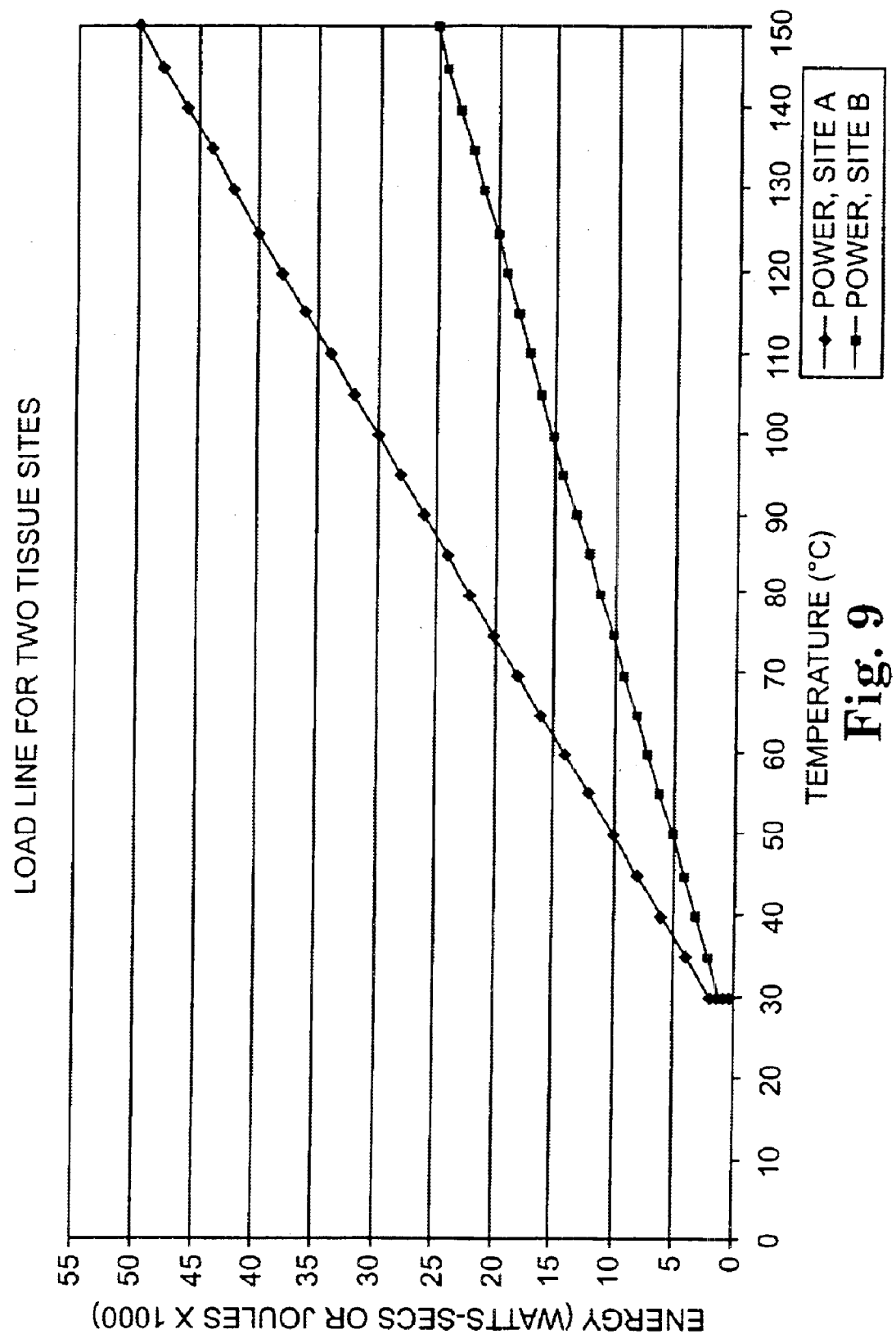
FIG. 9 is an exemplary graph of energy as a function of temperature for use in the method of the present invention.

A plurality of load lines within the range of tissue conductively expected to be encountered by system 11 are further stored in the memory of controller 16. A load line for each of exemplary sites A and B is shown in FIG. 9. Each load line represents the energy required to be provided to the first needle electrode 71 or the second needle electrode 73 so as to heat the targeted tissue to a desired temperature, measured by thermocouple 76 in the respective stylet 66 or 67, and to maintain the targeted tissue at such temperature for the duration of the contemplated procedure. The energy levels of FIG. 9 are empirically obtained for a variety of prostate types.

Figure 10:
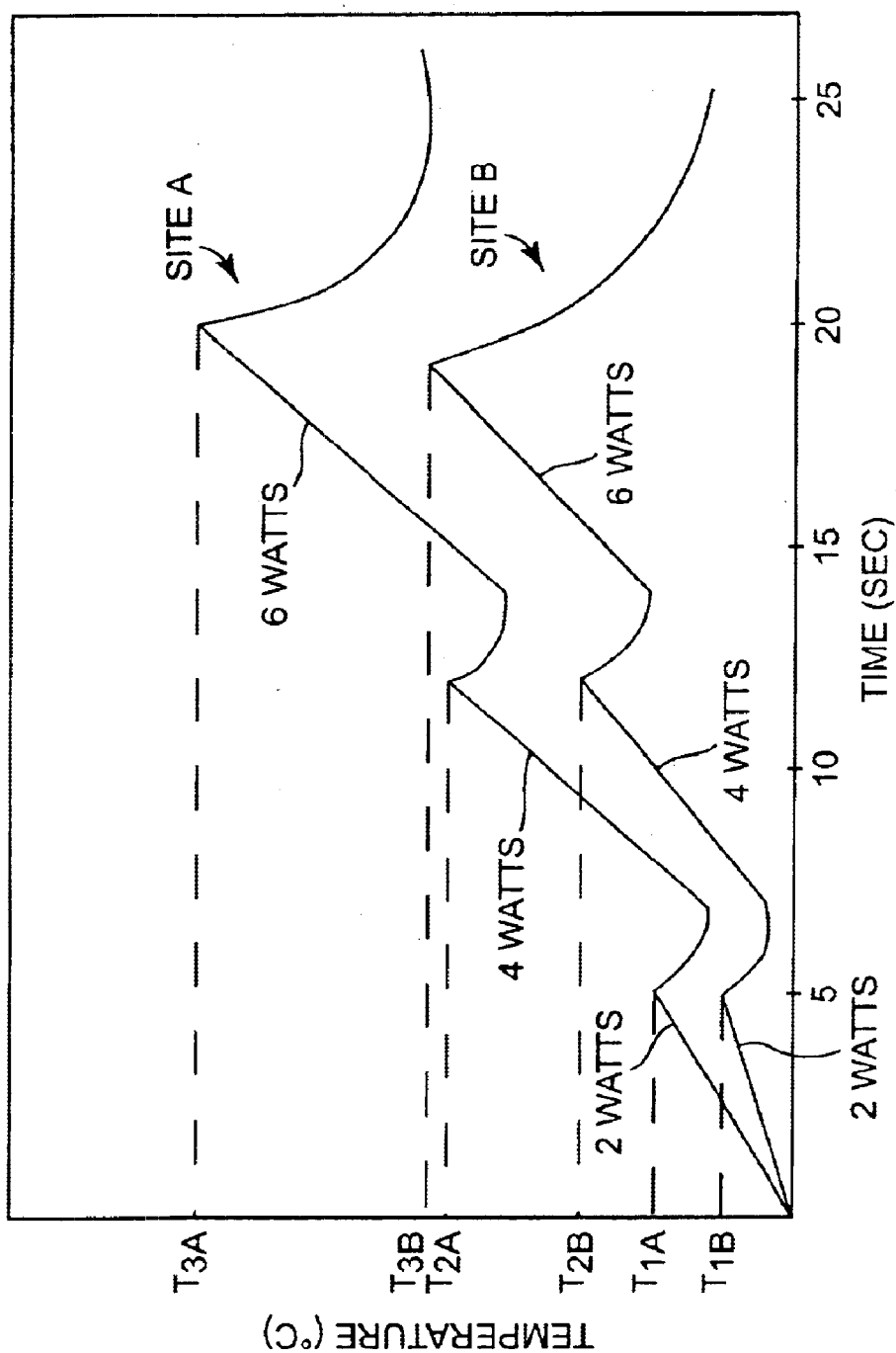
FIG. 10 is an exemplary graph of temperature as a function of time for use in the method of the present invention.

The tissue types examined for the purpose of FIG. 9 are further dynamically tested in the manner set forth in FIG. 10 and the information empirically obtained thereby stored in the computer memory 139 of controller 16. In one exemplary test procedure for obtaining data of the type shown in FIG. 10, for example at Site A, two watts of power is delivered to the tissue for a period of five seconds and the temperature $T_{1A}$ of the tissue at the end of such five seconds is measured. The delivery of power is stopped after five seconds, causing the temperature of the tissue to decay, as shown in FIG. 10. Thereafter, four watts of power is delivered to the tissue for a second five second period and the temperature $T_{2A}$ at the end of such five second period is measured. Power delivery is again interrupted for a predetermined period, In this instance two seconds, before six watts of power is delivered to the tissue for a third five second period and the resulting temperature $T_{3A}$ at the end of such period is measured. Similarly, empirical data for another tissue type, shown as Site B in FIG. 10, can be obtained and the temperatures $T_{1B}$, $T_{2B}$ and $T_{3B}$ stored in the computer memory 139. Each of the power levels supplied during this step are above the noise level of the power measuring instrument utilized. For each tissue type so examined, the computer of controller 16 correlates the static data of the FIG. 9 with the dynamic data of FIG. 10.

Figure 11:
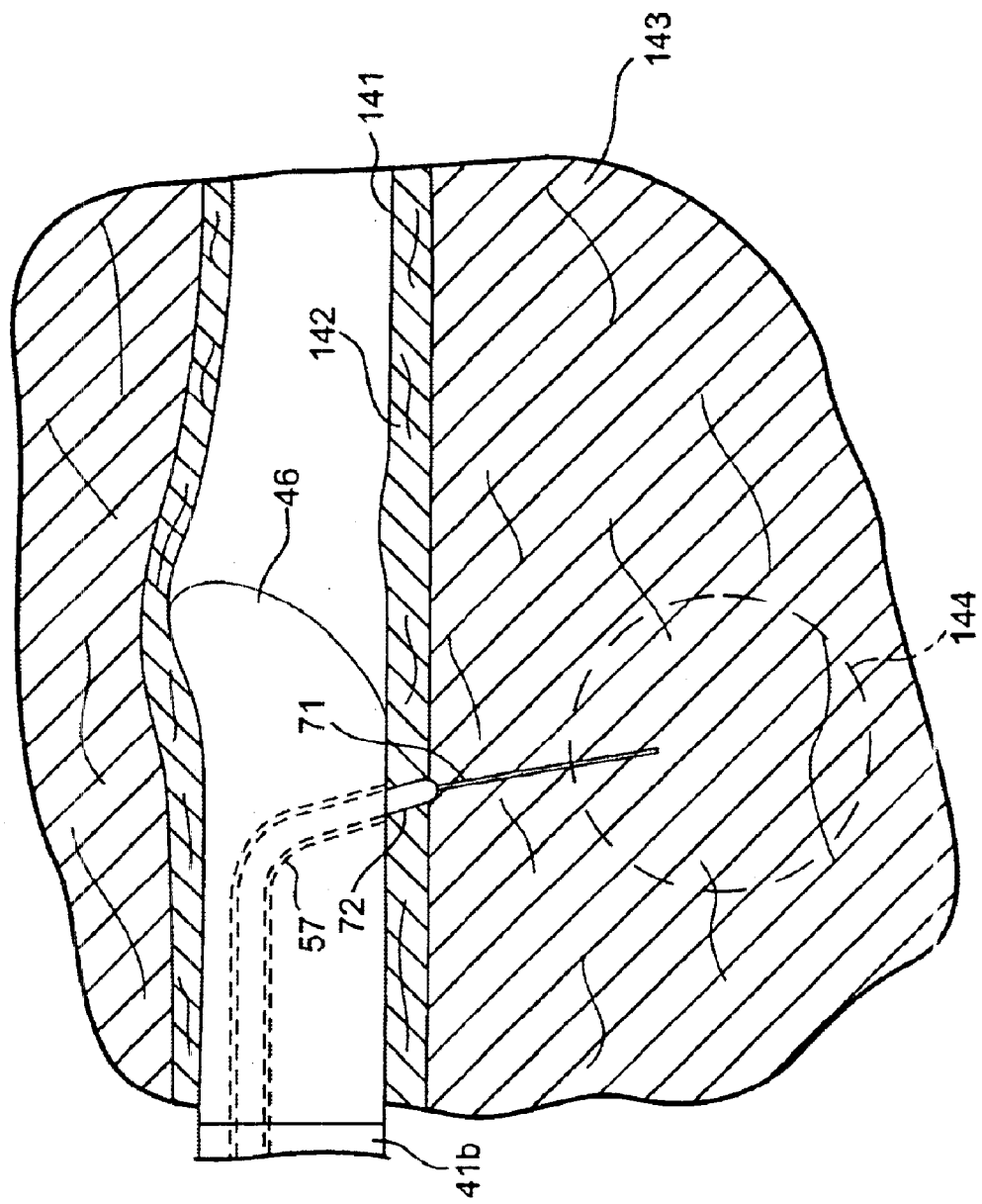
FIG. 11 is an enlarged view of the distal extremity of the apparatus of FIG. 1 treating targeted tissue in a procedure of the present invention.

In one method for treating tissue of the present invention, system 11 can be used to treat benign prostatic hyperplasia in a human male prostate. A portion of a urethra 141 of a human male, formed by a urethral wall 142 and surrounded by prostatic tissue 143, is shown in FIG. 11. A suitable procedure for treating a prostate of a human male is described in detail in U.S. Pat. Nos. 5,549,644 and 5,964,756, the entire contents of which are incorporated herein by this reference. In general, the distal extremity of torque tube 41 of apparatus 12 is introduced through the penis into the urethra 141 until distal tip 46 is in the vicinity of the prostate, as shown in FIG. 11. The operating physician then pulls down on trigger 91 to cause the first and second stylets 66 and 67 to deploy from distal tip 46. For simplicity, only first stylet 66 is shown in FIG. 11. The sharpened tips of first and second needle electrodes 71 and 73 penetrate the urethral wall 142 to permit the stylets to extend into the prostatic tissue 143. As discussed above, further downward movement of trigger 91 causes first and second sleeves 72 and 74 to retract relative to the electrodes. The sleeves, however, extend through the urethral wall 142 so as to protect the wall from radio frequency energy supplied to the needle electrodes 71 and 73.

Once the first and second stylet 76 and 67 have been so deployed in the prostatic tissue, system 11 automatically characterizes the conductivity of the prostatic tissue 143 in contact with the needle electrodes 71 and 73. In this regard, electromagnetic energy, and preferably radio frequency energy, is delivered to one of the first and second needle electrodes 71 and 73 at varying power levels and the temperature sensed by the thermocouple 76 corresponding to stylet 66 or 67 is measured by controller 16 after each such delivery of energy. More specifically, radio frequency energy is supplied to the needle electrode in a pulse to the prostatic tissue at a first power level and for a first length of time and thereafter the temperature of the prostatic tissue 143 is measured by the respective thermocouple 76. Radio frequency energy is then supplied to the needle electrode at a second power level and for a second period of time and the temperature of the prostatic tissue again measured by the thermocouple 76.

Although any suitable power level and time duration can be utilized, it is preferable that the method of characterizing the conductivity of the prostatic tissue be similar to the manner in which the dynamic empirical data of FIG. 10 was obtained. As a result, in one exemplary preferred method, two watts of power, four watts of power and six watts of power are sequentially delivered to the needle electrode for respective five second periods and the corresponding temperatures $T_1$, $T_2$ and $T_3$ of the prostatic tissue at the end of each such five second period are measured by the thermocouple 76 and retained by the controller 16. It should be appreciated that power can be delivered to more than one electrode, for example both needle electrodes 71 and 73, and temperatures adjacent such electrodes measured during the foregoing step of characterizing the conductivity of the tissue being treated.

The computer of control apparatus 16 is programmed to evaluate the sensed temperatures as a function of time and delivered power, that is energy, and determine which set of data similar to that shown in FIG. 10, and thus which load line stored in the memory of controller 16, is appropriate for the prostatic tissue being treated. The controller may determine that the load line for Site A, Site B or some other load line not shown on FIG. 9 best approximates the targeted tissue. In one preferred embodiment, the computer of controller 16 is programmed to choose the load line stored within its memory 139 that is nearest the load line calculated from the characterizing step exemplified by FIG. 9. In this manner, the operator can determine whether the targeted tissue is a wet or vascularized prostate, that may require relatively more energy for forming a desired lesion, or a dry or nonvascularized prostate, that may require relatively less energy for forming the desired lesion.

Although in the foregoing example, power is delivered to the first and second needle electrodes 71 and 73 in pulses of equal time duration, it should be appreciated that the power can be delivered in other than pulses. In addition, if pulses of power are utilized, such power pulses can be of equal time duration, as shown in FIG. 10, or of unequal time duration and be within the scope of the present invention. Further, pulses of power can be of any number in quantity and the power levels for the pulses can decrease or vary in any other manner throughout the characterizing step of the present invention. As discussed above, it is preferred that the methodology for dynamically characterizing the conductivity of the targeted tissue correspond to the methodology used in obtaining the information of FIG. 10 stored in the computer memory 139 of controller 16.

After the appropriate load line for the targeted tissue has been determined, the energy required to heat the targeted tissue adjacent each needle electrode to the desired temperature can be determined by such load line. For example, if the targeted tissue corresponds to Site A referred to in FIG. 9 and it is desired to heat the prostatic tissue adjacent each of the needle electrodes to 100° C., then FIG. 9 reveals that approximately 30,000 Watt-secs or Joules of energy must be delivered to each needle electrode 71 or 73. Alternatively, if the targeted tissue corresponds to Site B and it is desired to heat the targeted tissue to 100° C., then only 15,000 Joules is required for delivery to each of the needle electrodes. This determination step can be performed automatically by controller 16. In this regard, once the targeted temperature is inputted into the controller by the operating physician or otherwise, the processor within controller 16 accesses the appropriate load line corresponding to the targeted tissue and determines the energy required for delivery to each of the first and second stylets 66 and 67.

In the next step of the invention, the processor 138 of controller 16 retrieves from its memory 139 the optimal electrode volume corresponding to the tissue being treated. As discussed above, for example, FIG. 7 contains data for a sample tissue showing that the optimal electrode volume for maximizing the lesion volume in such tissue is 0.2 cubic millimeters. Such electrode volume provides an outer electrode surface area with an optimized current density that is high enough to maximize power delivery to the targeted tissue, but not so high as to cause tissue dehydration or charring that will create an undesirably high tissue impedance in the vicinity of the electrodes 71 and 73. Although the electrode volume can be assumed to have any shape, in one preferred method the electrode volume is assumed to be spherical or some other fixed shape so as to simplify the calculation of such optimal electrode volume.

Controller 16 next determines the duration of the procedure by dividing the power expected to be delivered throughout the procedure to a needle electrode into the aggregate energy required by the appropriate load line, as determined above, to be delivered to the targeted tissue. For example, if it has been determined from the load line that it is necessary to deliver 30,000 Joules of energy to each electrode to maintain the adjacent tissue at the desired temperature during the procedure and a constant 50 watts of power will be delivered to the needle electrode, then the duration of the procedure equals 30,000 watt-secs divided by 50 watts or 600 seconds. The controller can optionally retrieve from its computer memory 139 the temperature data similar to that of FIG. 8 so as to confirm that the optimal electrode volume determined above will provide the desired temperature in the targeted tissue when the expected power is delivered to the electrode. As discussed above for example, the information of FIG. 8 confirms that an electrode having a volume of 0.2 cubic millimeters will provide a temperature in excess of 100° C. when 50 watts of power is supplied to the electrode.

Controller 16 next determines the amount of conductive liquid to be supplied to the prostatic tissue, as a function of the conductivity of the tissue, to maintain such optimal wet electrode volume for each needle electrode 71 or 73 throughout the procedure. In one preferred embodiment, the controller 16 determines the rate at which the conductive liquid must be delivered to a needle electrode. Since in this example it has been determined that the optimal electrode volume is 0.2 cubic millimeters, the initial amount of conductive liquid to be supplied to each needle electrode is approximately 0.2 cubic millimeters. The amount of conductive liquid to be delivered for the duration of the procedure is dependent, at least in part, on the rate at which the liquid disperses or leaks away from the initial bolus of conductive liquid supplied to the targeted tissue. Although such leakage rate can range from 5% to 20% of the supplied conductive liquid, in one preferred method of the invention such leakage rate is assumed to be 15%. Accordingly, after the initial supply of liquid, additional conductive liquid is supplied at an infusion rate of 15% or 0.2 cubic millimeters per second or approximately 0.03 cubic millimeters per second for the remainder of the procedure. The initial amount of conductive liquid and the additional conductive liquid equal the aggregate conductive liquid supplied to the patient over an interval of time approximating the duration of the procedure. Where both needle electrodes 71 and 73 are utilized in the procedure, such amounts are delivered to each of the electrodes 71 and 73.

Controller 16 communicates with saline supply 17 to set the amount of conductive liquid and the infusion rate of such liquid to be supplied to the sleeve lumen 136 of each of the stylets 66 and 67 for forming the wet electrodes. One such wet electrode 144 is shown in FIG. 11. Once the desired wet electrode has been formed around each of the first and second stylets 66 and 67 by the initial supply of conductive liquid to the electrodes, the determined amount of constant radio frequency power is supplied by the radio frequency generator within controller 16 to each of the needle electrodes 71 and 73 for the prescribed time period calculated as above or otherwise. The controller can ramp quickly to such power level and then maintain such power level for the appropriate period of time. The exterior surface of the wet electrode serves as an outer electrode surface from which such radio frequency energy is delivered.

System 11 desirably provides an electrode device capable of delivering a conductive liquid adjacent to an electrode so as to effectively increase the surface area of the electrode. The relatively large surface area of the wet electrode of the present invention facilitates the creation of large lesions. In this regard, such large surface area is capable of supporting high levels of radio frequency current within an acceptably high current density range. Relatively high current densities at the outer surface of the wet electrode can advantageously cause heating and thus necrosis not only in the tissue adjacent the wet electrode, but also in tissue further from the periphery of the wet electrode. Undesirably high current densities, however, can cause tissue adjacent the needle to be heated to undesirably high temperatures, resulting in desiccation and in some instances charring of the tissue which increase the impedance of the tissue and can eventually create an undesirable electrical open electrical circuit.

The large surface area of the wet electrode of the invention permits the creation of large lesions in a shorter interval of time than an electrode having a smaller surface area. The relatively high power and current levels permitted by the large surface area contribute to such shorter procedure times. Additionally, the virtual or wet electrode of the present invention provides less trauma to the patient than a solid electrode of equal size.

System 11 efficiently delivers power to the ablation site and inhibits the delivery of undesirably high power levels which can cause undesirable pain to the patient. The system quickly ramps up to a maximum power level. Minimum current densities and temperatures to achieve lesion formation are reached. However, the system 11 inhibits the tissue temperature from reaching undesirably high temperatures and impedance levels where the effect of further inputted power is decreased.

The method of the invention quickly characterizes the conductivity of the targeted tissue by dynamically examining the targeted tissue over a relatively short period of time, for example approximately 20 seconds as shown in FIG. 10. The predetermined correlation of dynamic data similar to that of FIG. 10 with static data similar to that of FIG. 9 in the computer memory of the controller 16 enables the load line corresponding to the targeted tissue to be easily determined once the targeted tissue has been dynamically examined by applying a plurality of pulses of power to the tissue or otherwise.

The foregoing procedure of the invention has been described with the use of first and second stylets 66 and 67, however it should be appreciated that one or any plurality of stylets can be utilized. Although the method and apparatus of the invention have been described in connection with the treatment of the prostate, such method and apparatus can be used in any tissue of the body.

From the foregoing, it can be seen that a medical apparatus having a stylet capable of delivering a conductive liquid to tissue adjacent the stylet has been provided. The conductive liquid creates a wet electrode to effectively increase the ablative surface in the tissue. Such a wet electrode supports high radio frequency current levels and maintains sufficient current density to cause heating in the adjacent tissue.

What is claimed is:

1. A method for treating tissue of a mammalian body comprising the steps of:
   introducing a stylet into the tissue,
   supplying electromagnetic energy to the tissue,
   measuring the response of the tissue,
   then determining an amount of a conductive liquid to supply to the tissue as a function of the response of the tissue,
   injecting the amount of conductive liquid into the tissue through the stylet over an interval of time,
   determining an amount of energy to be delivered to the tissue, and
   supplying electromagnetic energy to the conductive liquid to form a lesion in the tissue.

2. The method of claim 1 wherein the electromagnetic energy is radio frequency energy.

3. The method of claim 1 wherein the response of the tissue comprises a temperature of the tissue.

4. The method of claim 3 wherein the steps of supplying electromagnetic energy to the tissue and measuring the response comprises the steps of:
   supplying radio frequency power to the tissue at a second power level and for a first length of time and thereafter measuring the temperature of the tissue, and
   supplying radio frequency power to the tissue at a second power level and for a second length of time and thereafter measuring the temperature of the tissue.

5. The method of claim 4 wherein the first length of time equals the second length of time.

6. The method of claim 1 wherein at least a portion of the injecting step and the supplying step occur simultaneously.

7. The method of claim 1 wherein the conductive liquid is a saline solution.

8. The method of claim 1 wherein the stylet includes a needle and a sleeve through which the needle extends, the injecting step including the step of injecting the amount of conductive liquid into the tissue through the sleeve.

9. The method of claim 1 wherein both supplying steps include supplying electromagnetic energy through the stylet.

10. The method of claim 1 wherein the supplying electromagnetic energy to the tissue step is accomplished through a needle electrode.

11. The method of claim 10 wherein the measuring step comprises measuring the thermal conductivity of the tissue.

12. The method of claim 10 wherein the measuring step comprises measuring at least one of the electrical impedance and electrical conductivity of the tissue.

13. The method of claim 1 wherein the determining an amount of a conductive liquid comprises determining a rate the conductive liquid is to be supplied to this tissue.

14. The method of claim 1 wherein the determining an amount of energy step comprises determining a rate at which energy is to be delivered to the tissue.

* * * * *